United States Patent
Woo et al.

(10) Patent No.: US 11,992,541 B2
(45) Date of Patent: May 28, 2024

(54) NANOEMULSION COSMETIC COMPOSITION AND PROCESS FOR PREPARING SAME

(71) Applicant: AMOREPACIFIC CORPORATION, Seoul (KR)

(72) Inventors: Byoung Young Woo, Yongin-si (KR); Yong Deog Hong, Yongin-si (KR); Joonyoung Hwang, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 17/512,347

(22) Filed: Oct. 27, 2021

(65) Prior Publication Data

US 2022/0125692 A1    Apr. 28, 2022

(30) Foreign Application Priority Data

Oct. 28, 2020    (KR) .................. 10-2020-0141310

(51) Int. Cl.
| | | |
|---|---|---|
| *A61K 8/06* | (2006.01) | |
| *A61K 8/92* | (2006.01) | |
| *A61K 8/9789* | (2017.01) | |
| *B82Y 5/00* | (2011.01) | |

(52) U.S. Cl.
CPC .............. *A61K 8/068* (2013.01); *A61K 8/922* (2013.01); *A61K 8/9789* (2017.08); *A61K 2800/21* (2013.01); *A61K 2800/413* (2013.01); *B82Y 5/00* (2013.01)

(58) Field of Classification Search
None
See application file for complete search history.

(56) References Cited

U.S. PATENT DOCUMENTS

2015/0327566 A1    11/2015   Epiphani

FOREIGN PATENT DOCUMENTS

| CN | 110179717 A | * | 8/2019 | .............. A61K 8/14 |
|---|---|---|---|---|
| CN | 110585029 A | * | 12/2019 | |
| FR | 2945936 A1 | | 12/2010 | |
| KR | 10-2003-0071485 A | | 9/2003 | |
| KR | 10-0833996 B1 | | 5/2008 | |
| KR | 10-2014-0000881 A | | 1/2014 | |
| KR | 10-2016-0134375 A | | 11/2016 | |
| KR | 10-2017-0108579 A | | 9/2017 | |
| KR | 10-1822003 B1 | | 1/2018 | |
| KR | 10-1894255 B1 | | 9/2018 | |
| KR | 10-2019-0085364 A | | 7/2019 | |
| KR | 10-2020-0060891 A | | 6/2020 | |
| KR | 10-2020-0076771 A | | 6/2020 | |

OTHER PUBLICATIONS

Young Sook Kim et al., "Differential Expression of Protein Kinase C Subtypes during Ginsenoside Rh2-Induced Apoptosis in SK-N-BE(2) and C6Bu-1 Cells", Arch Pharm Res, 23(5): 518-524 (2000).
Eiichi Tachikawa et al., "In vitro inhibition of adrenal catecholamine secretion by steroidal metabolites of ginseng saponins", Biochemical Pharmacology, 66(11): 2213-2221 (2003).
Shiow-Chwen Tsai et al., "Stimulation of the Secretion of Luteinizing Hormone by Ginsenoside-Rb1 in Male Rats", Chinese Journal of Physiology, 46(1): 1-7 (2003).
Shoji Shibata et al., "Chemistry and Cancer Preventing Activities of Ginseng Saponins and Some Related Triterpenoid Compounds", J Korean Med Sci, 16(Suppl): S28-37 (2001).
Hiroshi Saito et al., "Pharmacological Studies of Panax Ginseng Root : Estimation of Pharmacological Actions of Panax Ginseng Root", Japan. J. Pharmacol. 22: 245-259 (1972).
Search Report for European Patent Application No. 21204698.1. (Apr. 4, 2022).

* cited by examiner

*Primary Examiner* — Nannette Holloman
(74) *Attorney, Agent, or Firm* — Merchant & Gould P.C.

(57) ABSTRACT

The present disclosure relates to a nanoemulsion cosmetic composition including an oil phase and an aqueous phase, wherein the oil phase contains a ginseng nanopowder and an oil swollen by the ginseng nanopowder, the composition does not contain an additional surfactant, and the ginseng nanopowder is distributed uniformly in the composition. According to the present disclosure, there is provided a nanoemulsion cosmetic composition which contains a natural substance by containing a ginseng nanopowder and an oil swollen by the ginseng nanopowder in an oil phase and provides beneficial effect to skin.

11 Claims, 11 Drawing Sheets

NANOEMULSION COSMETIC COMPOSITION AND PROCESS FOR PREPARING SAME

CROSS-REFERENCE TO RELATED APPLICATION

This application claims priority to Korean Patent Application No. 10-2020-0141310, filed on Oct. 28, 2020, and all the benefits accruing therefrom under 35 U.S.C. § 119, the contents of which in its entirety are herein incorporated by reference.

BACKGROUND

1. Field

The present disclosure relates to a nanoemulsion cosmetic composition and a method for preparing the same.

2. Description of the Related Art

In a process of stably dispersing a liquid in another liquid for preparation of an emulsion, the addition of a surfactant is essential. In particular, in an oil-in-water emulsion, the surfactant surrounds oil droplets in a continuous aqueous phase, thereby providing a moist feel of use. However, there is a need of surfactant-free emulsions recently due to safety issue. Korean Patent Publication No. 10-2003-0071485 discloses an oil-in-water emulsion composition containing one or more oil component selected from a group consisting of a fatty acid and a higher alcohol and one or more polymer (polyvinylpyrrolidone or vinylpyrrolidone) which is soluble in the oil component but not containing a surfactant. However, it uses a chemically synthesized material and fails to provide a beneficial effect to skin. Therefore, research and development are required for an emulsion which contains a natural substance and provides a beneficial effect to skin.

SUMMARY

The present disclosure is directed to providing a nanoemulsion cosmetic composition which contains a natural substance and provides a beneficial effect to skin, and a method for preparing the same.

In an aspect, the present disclosure provides a nanoemulsion cosmetic composition including an oil phase and an aqueous phase, wherein the oil phase contains a ginseng nanopowder and an oil swollen by the ginseng nanopowder, the composition does not contain an additional surfactant, and the ginseng nanopowder is distributed uniformly in the composition. In another aspect, the present disclosure provides a method for preparing a nanoemulsion cosmetic composition, which includes preparing an emulsion through collision dispersion of water, an oil and a ginseng nanopowder precursor.

According to the present disclosure, there is provided a nanoemulsion cosmetic composition which contains a natural substance by containing a ginseng nanopowder and an oil swollen by the ginseng nanopowder in an oil phase and provides beneficial effect to skin.

DETAILED DESCRIPTION

The terms used in the present disclosure may be currently widely used general terms in consideration of the functions in the present disclosure but may vary depending on the intents of those skilled in the art, precedents or the advent of new technology. Additionally, in certain cases, there may be terms that the applicant selects arbitrarily. In this case, their meanings are described in detail in the corresponding description part of the present disclosure. Accordingly, the terms used in the present disclosure should be defined based on the meanings of the terms and the entire contents of the present disclosure rather than simply by the names of the terms.

All the terms including technical or scientific terms, unless defined otherwise, have the same meaning generally understood by those having ordinary knowledge in the art to which the present disclosure belongs. The generally understood terms are interpreted as having meanings identical to contextual meanings of the related art, unless definitely defined otherwise in the present disclosure, not as having ideal or excessively formal meanings.

Numerical ranges include the numerical values defined in the present disclosure. All maximum numerical limitations given throughout the present disclosure include all lower numerical limitations, as the lower numerical limitations are stated explicitly. All minimum numerical limitations given throughout the present disclosure include all higher numerical limitations, as the higher numerical limitations are stated explicitly. All numerical limitations given throughout the present disclosure will include any better numerical range within broader numerical ranges, as narrower numerical ranges are stated explicitly.

Hereinafter, the present disclosure is described specifically referring to examples and drawings. However, it is obvious that the present disclosure is not limited by the examples and drawings.

Figure 5:
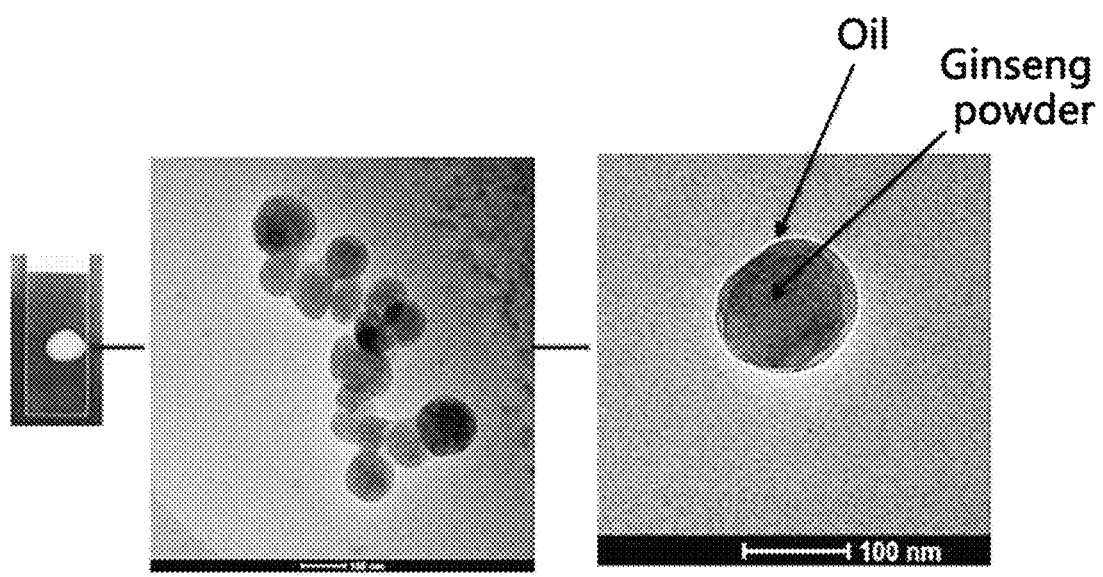
FIG. 5 shows the photographs of ginseng nanopowder and oil swollen by the ginseng nanopowder.

In an aspect, the present disclosure provides a nanoemulsion cosmetic composition including an oil phase and an aqueous phase, wherein the oil phase contains a ginseng nanopowder and an oil swollen by the ginseng nanopowder, the composition does not contain an additional surfactant, and the ginseng nanopowder is distributed uniformly in the composition. FIG. 5 shows the photographs of ginseng nanopowder and oil swollen by the ginseng nanopowder.

The "ginseng" may be Korean ginseng, or *Panax ginseng*. Ginseng is generally classified into fresh ginseng, white ginseng and red ginseng depending on its state. Fresh ginseng refers to a ginseng which has not been dried after being harvested and contains about 75 wt % of water, white ginseng refers to a ginseng which has been obtained by peeling and drying fresh ginseng, and red ginseng refers to a ginseng which has been obtained by steaming and drying fresh ginseng without peeling. In an exemplary embodiment, the ginseng may be one or more selected from a group consisting of the seed, root, stem, leaf and fruit of a plant in the genus *Panax*. Specifically, the plant in the genus *Panax* may be Korean ginseng (*Panax ginseng*), American ginseng (*Panax quinquefolius*), Chinese ginseng (*Panax notoginseng*), Japanese ginseng (*Panax japonicus*), dwarf ginseng (*Panax trifolium*), Himalayan ginseng (*Panax pseudoginseng*), Vietamese ginseng (*Panax vietnamensis*), etc. Depending on processing and growth environments, any of red ginseng, fresh ginseng, white ginseng, cultivated ginseng, cultivated wild ginseng, or wild ginseng including wild cultivated ginseng or cultured wild ginseng root may be used without limitation in varieties or kinds.

The "ginseng nanopowder" may be obtained by dry crushing or wet crushing of ginseng, such as sand milling, pearl milling, rod milling, pin milling, hammer milling, cutter milling, ball milling, jet milling, etc.

In an exemplary embodiment of the present disclosure, the ginseng nanopowder may be obtained from ginseng root. The ginseng root contains polysaccharide ingredients, especially pharmacologically active ginseng saponins, or ginsenosides.

Through many researches, the chemical structures of 37 ginsenosides have been identified. In addition, various pharmacological activities including anti-stress effects, brain cell-protecting effects, antithrombotic effects, lipid metabolism-improving effects, cancer cell proliferation-inhibiting effects, antidiabetic effects, anti-fatigue effects, etc. have been identified through basic researches [*Arch. Pharm. Res.* 2000, Oct., 23 (5) 518-524, *Biochem Pharmacol.* 2003 Dec. 1; 66 (11): 2213-21. Chin *J Physiol.* 2003 Mar. 31; 46 (1): 1-7., Shibata et al. *J. Korean Med Sci.* 16 (suppl.) S28-37 (2001)].

Ginsenosides are neutral bisdesmoside glycosides wherein sugar molecules such as glucose, arabinose, xylose, rham nose, etc. are bound to a triterpenoid-based dammarane backbone. They are classified into panaxadiol-, panaxatriol- and oleanane-based ginsenosides depending on the positions where the sugar molecules are attached and the shape of the backbone structure, and they show different pharmacological activities in the body. In particular, it is reported that the panaxatriol-based ginsenosides have blood pressure-raising, body temperature-elevating and central nervous system-exciting effects, whereas the panaxadiol-based ginsenosides have blood pressure-lowering, body temperature-lowering and nervous system-relaxing effects [Saito et al. *Jap. Pham.* 22: 245-259 (1972)]. The representative examples of the panaxatriol-based ginsenosides are ginsenosides Rg1 and Re, and the representative examples of the panaxadiol-based ginsenosides are ginsenosides Rb1 and Rd.

In an exemplary embodiment of the present disclosure, the composition does not contain an additional surfactant. The presence of a surfactant is disadvantageous in that a cosmetic composition should be prepared under a mild condition and the use of an activator, particularly a heat-sensitive activator, is precluded. In addition, the surfactant may be irritant to users having sensitive skin. Therefore, cosmetic compositions requiring minimized or no use of surfactants are being studied consistently. The present disclosure provides a composition which is dispersed stably although it is substantially free of a surfactant, which is possible due to aqueous counter collision during the preparation of the composition, the kinds and contents of the ingredients of the composition, etc.

The expression "substantially free of a surfactant" means that the presence of a synthetic surfactant component can be minimized or excluded. It means that the surfactant is contained in an amount of 1% or less, specifically 0.5% or less, more specifically 0.1% or less, based on the total weight of the composition.

The "oil phase" refers to a phase which is not mixed well with an aqueous phase. It may be an oil, organic solvent, a mixture thereof, etc., which is a liquid at room temperature and atmospheric pressure. The "aqueous phase" refers to a phase which is not mixed well with an oil phase. It may be any one which can dissolve a water-soluble polymer well, without limitation. Examples may include water such as purified water or distilled water, polyols, etc.

The oil may be any common oil component without limitation. It may be one or more oil selected from a hydrocarbon-based oil, a higher fatty alcohol-based oil, a glyceride-based oil, a silicone-based oil, an ester-based oil, a fluorine-based oil, a natural oil (vegetable oil, animal oil, etc.), etc. Specifically, it may be a natural oil. In an exemplary embodiment of the present disclosure, the oil included in the oil phase is ginseng seed oil. The ginseng seed oil is composed mostly of unsaturated fatty acids, more specifically oleic acid, linoleic acid, etc. The nanoemulsion cosmetic composition of the present disclosure is a nanoemulsion cosmetic composition including an oil phase and an aqueous phase, wherein a ginseng nanopowder and an oil swollen by the ginseng nanopowder are included in the oil phase. A saponin-based compound may be distributed at the interface between the oil phase and the aqueous phase. Furthermore, the composition may be a so-called "whole cosmetic composition" wherein the oil in the oil phase is ginseng seed oil derived from ginseng. The "whole cosmetic composition" refers to a cosmetic composition consisting of naturally derived ingredients, without containing harmful additives such as artificial preservatives, artificial colorants, etc.

In an exemplary embodiment of the present disclosure, the oil phase is included in an amount of 4-20 wt %, more specifically 4 wt % or more, 4.65 wt % or more, 5 wt % or more, 5.83 wt % or more, 6 wt % or more, 6.66 wt % or more, 7 wt % or more, 8 wt % or more, 9 wt % or more, or 10 wt % or more; and 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, or 10 wt % or less, based on the total weight of the composition, although not being limited thereto.

In an exemplary embodiment of the present disclosure, the oil phase has an average diameter of 500 nm or less, more specifically 500 nm or less, 450 nm or less, 400 nm or less, 350 nm or less, 300 nm or less, 250 nm or less, 200 nm or less, or 150 nm or less. The lower limit of the average diameter of the oil phase is not specially limited and may be determined adequately by those skilled in the art. When the average diameter of the oil phase is equal to or less than the upper limit, elegant appearance can be provided and uniform and soft sense of touch can be provided when applied to skin.

In an exemplary embodiment of the present disclosure, the oil is contained in an amount of 2.5 wt % or more and 15 wt % or less, more specifically 2.5 wt % or more, 2.65 wt % or more, 3 wt % or more, 3.5 wt % or more, 4 wt % or more, 4.76 wt % or more, 5 wt % or more, 6 wt % or more, 7 wt % or more, 8 wt % or more, 9 wt % or more, or 10 wt % or more; and 15 wt % or less, 14.5 wt % or less, 14 wt % or less, 13.5 wt % or less, 13 wt % or less, 12.5 wt % or less, 12 wt % or less, 11.5 wt % or less, 11 wt % or less, 10.5 wt % or less, or 10 wt % or less, based on the total weight of the composition, although not being limited thereto.

In an exemplary embodiment of the present disclosure, the ginseng nanopowder is contained in an amount of more than 0 wt % and 5 wt % or less, more specifically more than 0 wt %, 0.1 wt % or more, 0.5 wt % or more, 1 wt % or more, 1.5 wt % or more, 1.9 wt % or more, 2 wt % or more, 2.5 wt % or more, 3 wt % or more; and 5 wt % or less, 4 wt % or less, or 3 wt % or less, based on the total weight of the composition, although not being limited thereto.

In the composition of the present disclosure, a saponin-based compound may be distributed at the interface between the oil phase and the aqueous phase. In an exemplary embodiment of the present disclosure, the saponin-based compound is derived from the ginseng nanopowder. More specifically, the saponin-based compound distributed at the interface between the oil phase and the aqueous phase is released from the ginseng nanopowder and arranged at the interface between the oil phase and the aqueous phase. As a natural substance serving as a surfactant by containing both hydrophilic and hydrophobic groups, the saponin-based compound forms a stable dispersed phase via a combination of the saponin-based compound and the oil. The saponin-based compound exerts effective surfactant effect, which is derived from aqueous counter collision during the preparation of the composition, the kinds and contents of the ingredients of the composition, etc.

In an exemplary embodiment of the present disclosure, the ginseng nanopowder is distributed uniformly in the composition. Although the formulation of the composition of the present disclosure is not specially limited, it may be an oil-in-water type wherein a microphase surrounded by the saponin-based compound is an oil particle or a water-in-oil wherein a microphase surrounded by the saponin-based compound is a water particle. In an exemplary embodiment of the present disclosure, the composition may be an oil-in-water type. The formulation and type of the composition of the present disclosure may be prepared by adjusting the components of the saponin-based compound, the arrangement of the saponin-based compound and the condition of aqueous counter collision for preparation of the composition.

In an exemplary embodiment of the present disclosure, the ginseng nanopowder is contained in an amount of 1 wt % or more and 5 wt % or less, more specifically 1 wt % or more, 1.5 wt % or more, 1.9 wt % or more, 2 wt % or more, 2.5 wt % or more, or 3 wt % or more; and 5 wt % or less, 4.5 wt % or less, 4 wt % or less, 3.5 wt % or less, or 3 wt % or less, based on the total weight of the composition, although not being limited thereto. The content of the ginseng nanopowder refers to a weight including the saponin-based compound released from the ginseng nanopowder.

In an exemplary embodiment of the present disclosure, the ginseng nanopowder and the oil are contained at a ratio of 1:1-3, more specifically 1:1 or more, 1:1.1 or more, 1:1.2 or more, 1:1.3 or more, 1:1.33 or more, 1:1.4 or more, 1:1.5 or more, 1:1.6 or more, 1:1.7 or more, 1:1.8 or more, 1:1.9 or more, or 1:2 or more; and 1:3 or less, 1:2.9 or less, 1:2.8 or less, 1:2.7 or less, 1:2.6 or less, 1:2.51 or less, 1:2.5 or less, 1:2.4 or less, 1:2.3 or less, 1:2.2 or less, 1:2.1 or less, or 1:2 or less, based on weight, although not being limited thereto.

In an exemplary embodiment of the present disclosure, the composition may be formulated by a common method. For the formulation, the International Cosmetic Ingredient Dictionary published by the Cosmetic, Toiletry and Fragrance Association may be consulted.

Specifically, the composition may be formulated into a softening lotion, a nourishing lotion, an essence, a mist, etc.

Depending on the quality or function of the final product, the composition may further contain an adjuvant commonly used in the field of cosmetology or dermatology such as a fatty substance, an organic solvent, a solubilizer, a thickener, a gelling agent, a softening agent, an antioxidant, a suspending agent, a stabilizer, a foaming agent, an aromatic, antiseptic, pH control agent, water, ionic or nonionic emulsifier, filler, metal ion sequestrant, chelating agent, preservative, blocker, wetting agent, essential oil, dye, pigment, hydrophilic or oleophilic activator, if necessary.

In another aspect, the present disclosure provides a method for preparing a nanoemulsion cosmetic composition, which includes preparing an emulsion through collision dispersion of water, an oil and a ginseng nanopowder precursor.

As the water, clean water, purified water, hard water, soft water, natural water, deep sea water, electrolytic alkali ion water, electrolytic acid ion water, ionized water or cluster water may be used, although not being limited thereto.

In an exemplary embodiment of the present disclosure, the oil is contained in an amount of 2.5 wt % or more and 15 wt % or less, more specifically 2.5 wt % or more, 2.65 wt % or more, 3 wt % or more, 3.5 wt % or more, 4 wt % or more, 4.76 wt % or more, 5 wt % or more, 6 wt % or more, 7 wt % or more, 8 wt % or more, 9 wt % or more, or 10 wt % or more; and 15 wt % or less, 14.5 wt % or less, 14 wt % or less, 13.5 wt % or less, 13 wt % or less, 12.5 wt % or less, 12 wt % or less, 11.5 wt % or less, 11 wt % or less, 10.5 wt % or less, or 10 wt % or less, based on the total weight of the composition, although not being limited thereto.

In an exemplary embodiment of the present disclosure, the ginseng nanopowder precursor is contained in an amount of more than 0 wt % and 5 wt % or less, more specifically more than 0 wt %, 0.1 wt % or more, 0.5 wt % or more, 1 wt % or more, 1.5 wt % or more, 1.9 wt % or more, 2 wt % or more, 2.5 wt % or more, or 3 wt % or more; and 5 wt % or less, 4 wt % or less, or 3 wt % or less, based on the total weight of the composition, although not being limited thereto.

In an exemplary embodiment of the present disclosure, the collision dispersion refers to collision of a solution wherein water, an oil and a ginseng nanopowder precursor are dispersed by spraying using opposing nozzles. The method of spraying and collision is also called aqueous counter collision. The method is environment-friendly because no additional solvent is used other than water and is economical because post-treatment owing to the use of a solvent is not necessary.

In an exemplary embodiment of the present disclosure, the angle between the opposing nozzles may be 140°-170°, more specifically 140° or more, 145° or more, 150° or more, or 155° or more; and 170° or less, 165° or less, 160° or less, or 155° or less, although not being limited thereto.

In an exemplary embodiment of the present disclosure, the number of collision may be 30-40 times, more specifically 30 or more times, 31 or more times, 32 or more times, 33 or more times, 34 or more times or 35 or more times; and 40 or less times, 39 or less times, 38 or less times, 37 or less times, 36 or less times, or 35 or less times, although not being limited thereto.

In an exemplary embodiment of the present disclosure, the diameter of the nozzle may be 0.2-0.45 mm, more specifically 0.2 mm or more, 0.25 mm or more, or 0.3 mm or more; and 0.45 mm or less, 0.4 mm or less, 0.35 mm or less, or 0.3 mm or less, although not being limited thereto.

A spray collision pressure may be 180-200 MPa, more specifically 180 MPa or more, 182 MPa or more, 184 MPa or more, 186 MPa or more, 188 MPa or more, or 190 MPa or more; and 200 MPa or less, 198 MPa or less, 196 MPa or less, 194 MPa or less, 192 MPa or less, or 190 MPa or less, although not being limited thereto.

As a result of the collision under high pressure, the ginseng nanopowder precursor is crushed further and a ginseng nanopowder is formed. The size of the ginseng nanopowder may be controlled by controlling the angle between the opposing nozzles, the spray collision pressure, the number of collisions, etc. Meanwhile, since the temperature of the dispersion is increased rapidly due to the collision, a cooling system may be used to maintain a constant temperature.

In an exemplary embodiment of the present disclosure, the oil is ginseng seed oil. As described above, the nanoemulsion cosmetic composition of the present disclosure contains a ginseng nanopowder in the oil phase and, a "whole cosmetic composition" may be formed when the oil constituting the oil phase is ginseng seed oil derived from ginseng.

In an exemplary embodiment of the present disclosure, the ginseng nanopowder precursor may be obtained without an extraction process using a solvent. In an exemplary embodiment of the present disclosure, the ginseng nanopowder precursor include particles with a volume-based particle size distribution, D90, measured by laser diffractometry of less than 16 μm.

Laser diffractometry is a method of determining the size distribution or diameter distribution of particles. The "Dx according to a volume-based particle diameter distribution" determined by the measurement method refers to a diameter corresponding to a cumulative volume percentage x % in a volume-based particle size distribution chart. The Dx may be also expressed by [$D_x$], $D_{[x]}$, [Dx], D(0.x), D[0.x], etc.

Accordingly, D50 according to a volume-based particle diameter distribution refers to a diameter corresponding to a cumulative volume percentage 50% in a volume-based particle size distribution chart. Likewise, D90 according to a volume-based particle diameter distribution refers to a diameter corresponding to a cumulative volume percentage 90% in a volume-based particle size distribution chart.

Specifically, the D90 of the ginseng nanopowder precursor may be more than 7 μm, 7.5 μm or more, 8 μm or more, 8.5 μm or more, 9 μm or more, 9.5 μm or more, 10 μm or more, 10.5 μm or more, 11 μm or more, 11.5 μm or more, 12 μm or more, or 12.4 μm or more; and less than 16 μm, 15.5 μm or less, 15 μm or less, 14.5 μm or less, 14 μm or less, 13.5 μm or less, 13 μm or less, 12.5 μm or less, or 12.4 μm or less.

EXAMPLES

Hereinafter, the present disclosure is described in detail through examples. However, the following examples are provided only as examples for helping understanding of the present disclosure, and the content of the present disclosure is not limited by the examples.

<Preparation Example 1> Preparation of Ginseng Nanopowder Precursor

A coarsely crushed ginseng nanopowder was obtained by coarsely crushing dried ginseng (O'Sulloc Farm, Korea) root using a cutting mill (SM100, Retsch, cutting speed: 1,500 min$^{-1}$). Then, a ginseng nanopowder precursor was obtained by supplying the coarsely crushed ginseng nanopowder to an air jet mill (SD Micronizer, Sturevant) at a speed of 3 g/min and inducing collision using an ultrasonic air flow of 3 g/min.

Figure 1:
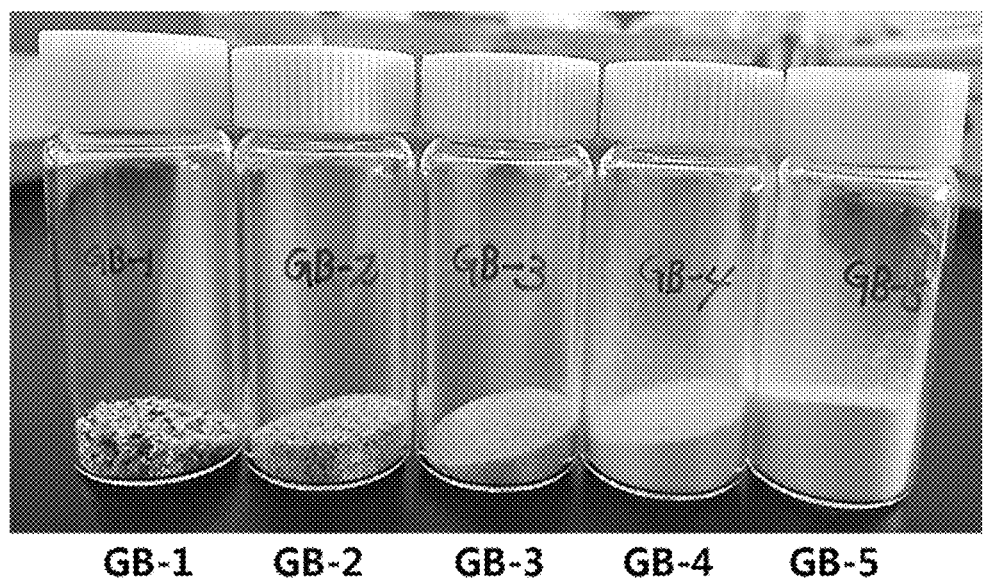
FIG. 1 shows the photographs of ginseng nanopowder precursors used to prepare compositions according to an exemplary embodiment.

<Test Example 1> Evaluation of Oil Absorption Depending on Particle Size of Ginseng Nanopowder Precursor 1. Sample Preparation Ginseng nanopowder precursors with D90 of 1470 μm (GB-1), 446 μm (GB-2), 176 μm (GB-3), 14 μm (GB-4) and 10 μm (GB-5) were prepared by controlling air jet milling time and using a particle classifier (AS 200 jet, Retsch) (FIG. 1). The particle size was analyzed using a particle size analyzer (Mastersizet 2000, Malvern Panalytical).

2. Evaluation Method

Oil absorption by GB-1, GB-2, GB-3, GB-4 and GB-5 was measured according to "General methods for testing pigments and extender pigments, Part 5: Measurement of oil absorption)" of Korean Industrial Standards (KS) KS M ISO 787-5:2007 (JIS K 5107, 1978). The test method can be consulted in "http://www.kssn.net/StdKS/ks_detail.asp?k1=M&k2=ISO %20787-5&k3=2", which is incorporated herein in its entirety.

More specifically, the oil absorption (g/g) is measured as follows.

1) 1.00 g of ginseng nanopowder precursor is weighed on a Petri dish.
2) The weight of syringe+CSA (caprylic/capric triglyceride) is measured.
3) Adequate amounts of the CSA of 2) and the precursor of 1) are added using a syringe.
4) The powder of 3) is mixed with an oil using a spatula.
5) The processes of 2) and 3) are repeated until the powder of 3) is conglomerated by the oil.
6) The amount of the oil is measured by measuring the weight of syringe+CSA.

Figure 2:
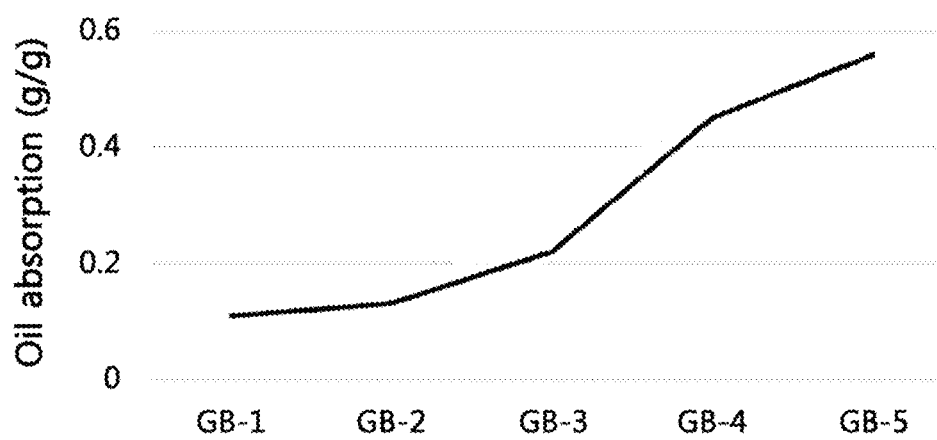
FIG. 2 shows a result of evaluating oil absorption by ginseng nanopowder precursors used to prepare compositions according to an exemplary embodiment.

The result is shown in Table 1 and FIG. 2.

TABLE 1

|  | GB-1 | GB-2 | GB-3 | GB-4 | GB-5 |
| --- | --- | --- | --- | --- | --- |
| Oil absorption (CSA g/g) | 0.11 | 0.13 | 0.22 | 0.45 | 0.56 |

3. Evaluation Result

From Table 1 and FIG. 2, it can be seen that the oil absorption by the ginseng nanopowder precursors GB-4 and GB-5, with D90 of less than 16 μm, was 0.45 and 0.56, respectively, confirming that the oil absorption is increased as the particle size is decreased when compared with the ginseng nanopowder precursors GB-1, GB-and GB-3, with D90 of 1470 μm, 446 μm and 176 μm, respectively.

<Preparation Example 2> Preparation of Nanoemulsion Composition 2.4 L of purified water, 450 g of ginseng seed oil and 150 g of the ginseng nanopowder precursor prepared in Preparation Example 1 were collided by aqueous counter collision by spraying using opposing nozzles. Spray collision pressure was 200 MPa and the collision was repeated 30 times. The prepared compositions are described in Table 2 (unit: wt %; Oil/P: ratio of ginseng seed oil/ginseng nanopowder precursor; P %: total content of ginseng nanopowder precursor).

TABLE 2

|  | Ginseng nanopowder precursor | Ginseng seed oil | Water | Oil/P | P % |
|---|---|---|---|---|---|
| Comp. Ex. 1 | 10 | 0 | Rest | 0.00 | 11.01 |
| Comp. Ex. 2 | 10 | 5 | Rest | 0.50 | 10.30 |
| Comp. Ex. 3 | 8 | 24 | Rest | 3.00 | 6.81 |
| Comp. Ex. 4 | 8 | 16 | Rest | 2.00 | 7.23 |
| Comp. Ex. 5 | 7 | 21 | Rest | 3.00 | 5.98 |
| Comp. Ex. 6 | 7 | 14 | Rest | 2.00 | 6.29 |
| Comp. Ex. 7 | 5 | 20 | Rest | 4 | 5.26 |
| Ex. 1 | 5 | 15 | Rest | 3 | 5.26 |
| Ex. 2 | 5 | 10 | Rest | 2 | 5.26 |
| Ex. 3 | 5 | 5 | Rest | 1.00 | 5.26 |
| Ex. 4 | 1.9 | 4.76 | Rest | 2.51 | 1.94 |
| Ex. 5 | 2 | 4 | Rest | 2.00 | 2.04 |
| Ex. 6 | 3 | 4 | Rest | 1.33 | 3.09 |
| Ex. 7 | 2.5 | 3.33 | Rest | 1.33 | 2.56 |
| Ex. 8 | 2 | 2.65 | Rest | 1.33 | 2.04 |

<Test Example 2> Evaluation of Stability of Compositions of Examples and Comparative Examples 1. Evaluation Method For the compositions of Examples and Comparative Examples of Preparation Example 2, formulation stability was evaluated by visually observing the degree of separation of the aqueous phase and the oil phase. The result is shown in Table 3 (o: dispersion, Δ: precipitation, X: separation, ΔX: precipitation and separation).

TABLE 3

|  | Comp. Ex. 1 | Comp. Ex. 2 | Comp. Ex. 3 | Comp. Ex. 4 | Comp. Ex. 5 | Comp. Ex. 6 | Comp. Ex. 7 | — |
|---|---|---|---|---|---|---|---|---|
| Stability | Δ | Δ | Δ X | Δ | Δ X | Δ | Δ X | — |
|  | Ex. 1 | Ex. 2 | Ex. 3 | Ex. 4 | Ex. 5 | Ex. 6 | Ex. 7 | Ex. 8 |
| Stability | ○ | ○ | ○ | ○ | ○ | ○ | ○ | ○ |

2. Evaluation Result

As seen from Table 3, Examples 1-8 with Oil/P (ratio of ginseng seed oil/ginseng nanopowder precursor) and P % (total content of ginseng nanopowder precursor) of preferred ranges showed superior stability.

<Test Example 3> Measurement of Size of Oil Phase 1

1. Evaluation Method

Compositions of Example 9, Example 10 and Example 11 were prepared in the same manner as Example 1 except that the pressure of the opposing nozzles was changed to 160 MPa, 180 MPa and 200 MPa, respectively. The average (Z-average) diameter of the oil phase in the compositions of Example 9, Example 10 and Example 11 was investigated using a NanoBrook Omni particle size analyzer (Malvern-Panalytical). The result is shown in Table 4 and FIG. 3.

TABLE 4

|  | (Unit: nm) | | |
|---|---|---|---|
|  | Ex. 9 | Ex. 10 | Ex. 11 |
| Average diameter | 275.6 | 218.2 | 165.6 |

2. Evaluation Result

Figure 3A:
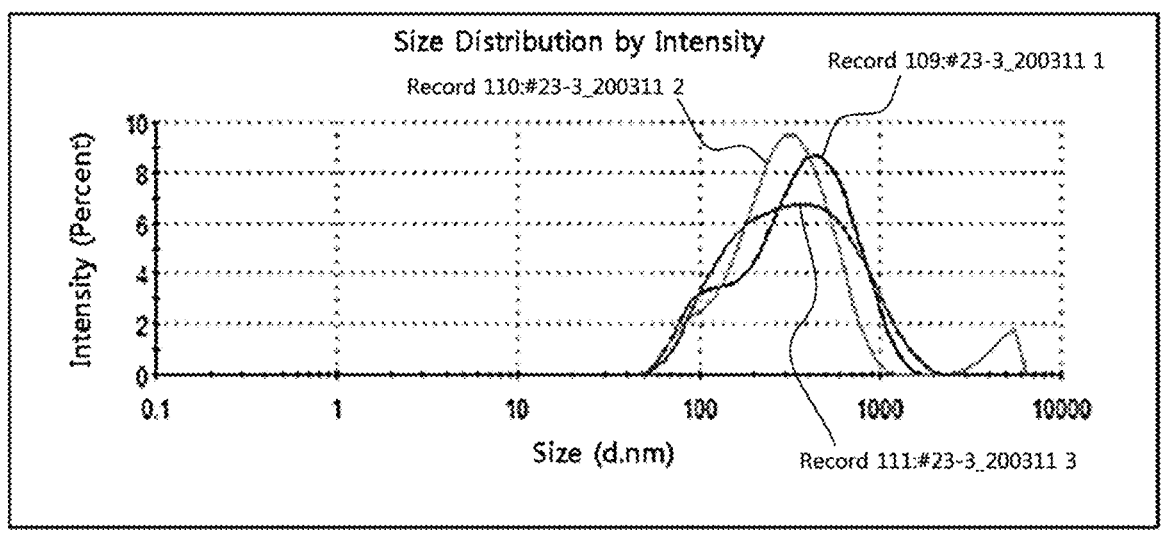
FIGS. 3A-3C and 4A-4E show a result of measuring the size of oil phases of compositions according to an exemplary embodiment.
Figure 3B:
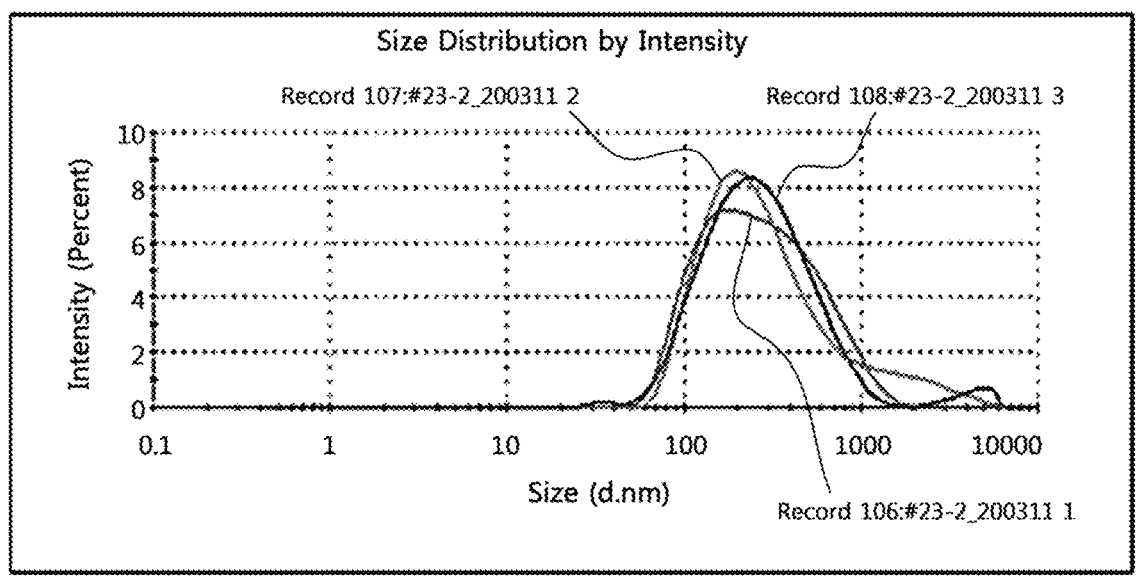
Figure 3C:
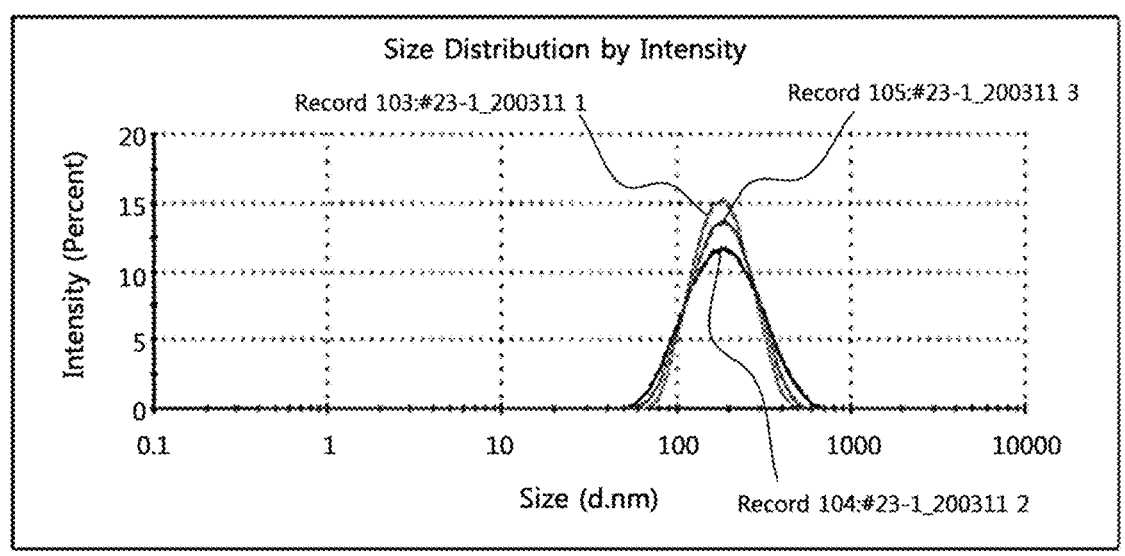
Figure 4A:
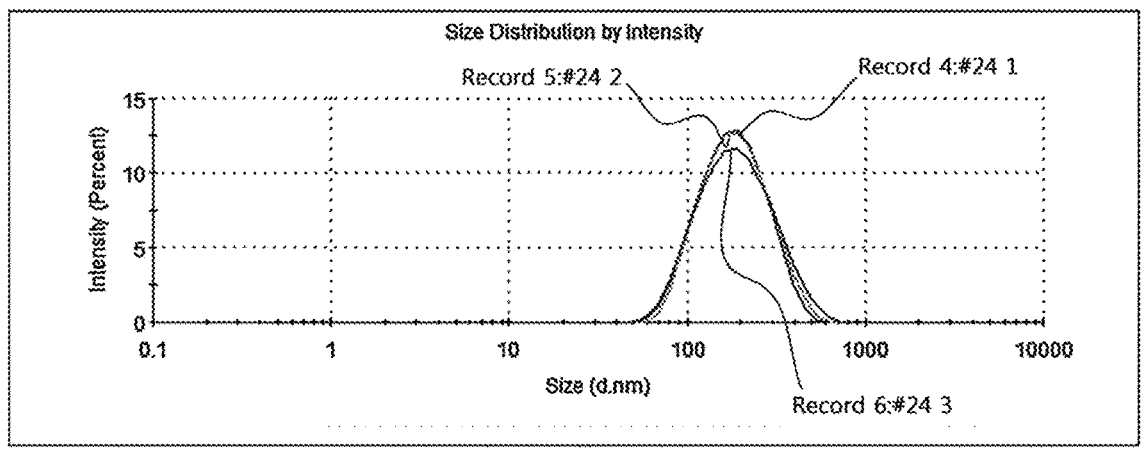
Figure 4B:
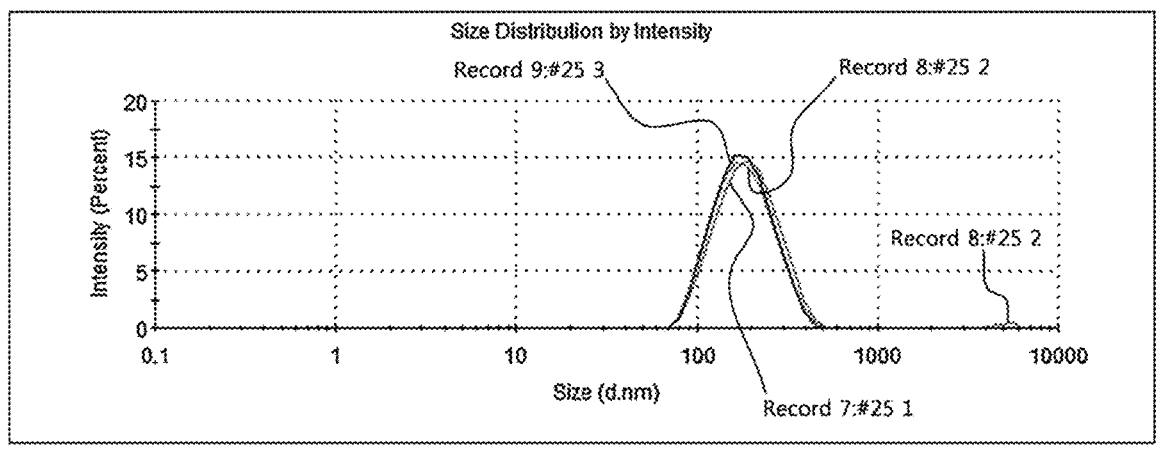
Figure 4C:
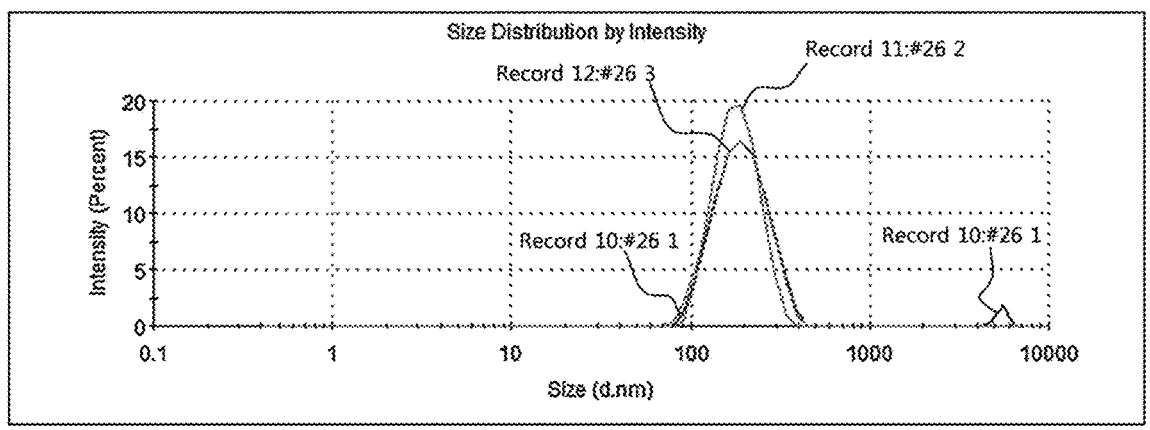
Figure 4D:
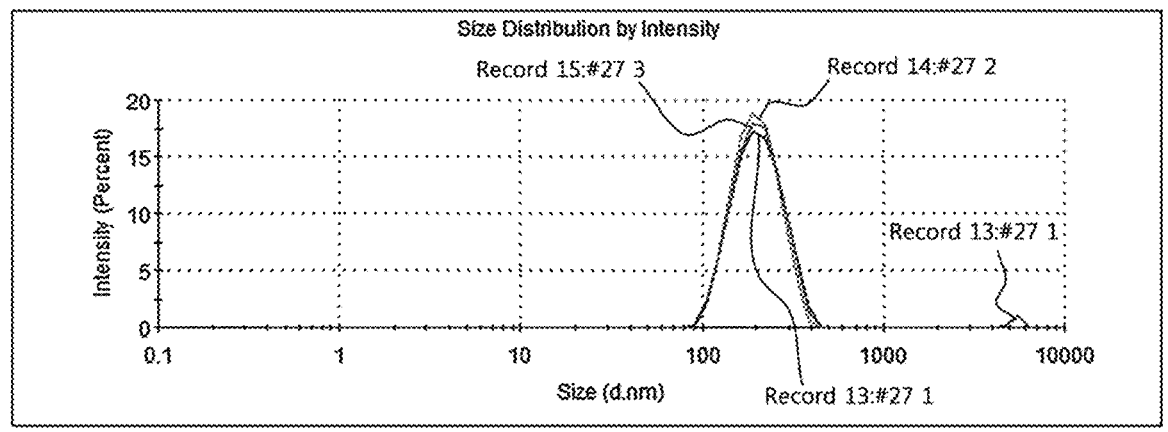
Figure 4E:
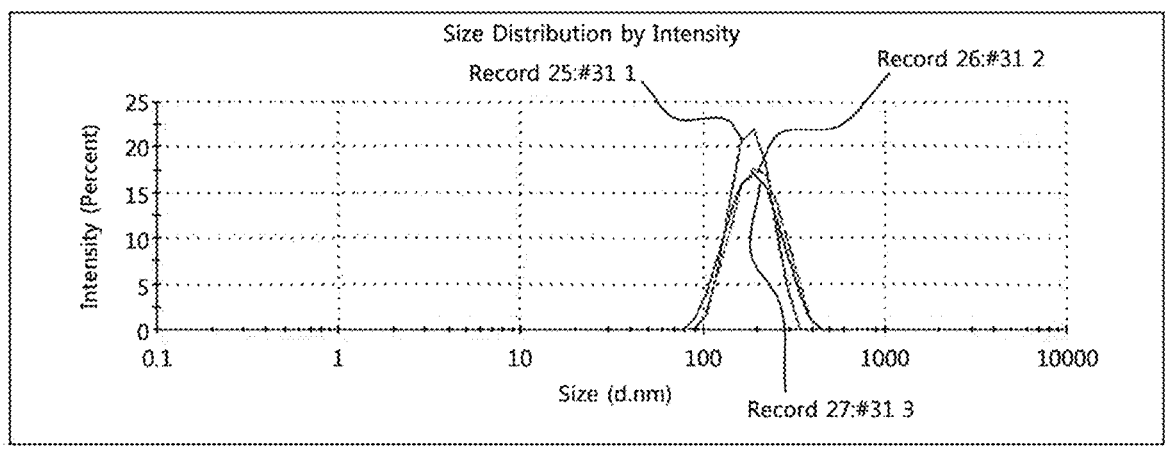

As seen from Table 4 and FIG. 3, compositions with the average (Z-average) diameter of the oil phase of 275.6 nm, 218.2 nm and 165.6 nm could be obtained when the pressure of the opposing nozzles was 160 MPa, 180 MPa and 200 MPa, respectively. Through this, it can be seen that the size of the oil phase of the composition can be controlled by controlling the collision pressure of opposing nozzles in aqueous counter collision.

<Preparation Example 3> Preparation of Nanoemulsion Cosmetic Composition

Nanoemulsion cosmetic compositions of Examples 12-16 were prepared in the same manner as in Example 1 except that the contents of the ginseng seed oil and the ginseng nanopowder precursor were adjusted and an adjuvant commonly used in the field of cosmetology was added. The compositions are described in Table 5 (unit: wt %).

TABLE 5

|  | (Unit: wt %) | | | | |
|---|---|---|---|---|---|
|  | Ex. 12 | Ex. 13 | Ex. 14 | Ex. 15 | Ex. 16 |
| Ginseng seed oil | 0.40 | 0.80 | 1.20 | 1.60 | 2.40 |
| Ginseng nanopowder precursor | 0.20 | 0.40 | 0.60 | 0.80 | 1.20 |
| 1,3-Propanediol | 20.0 | 20.0 | 20.0 | 20.0 | 20.0 |
| 1,2-Hexanediol | 2.0 | 2.0 | 2.0 | 2.0 | 2.0 |
| Ethylhexylglycerin | 0.05 | 0.05 | 0.05 | 0.05 | 0.05 |
| Purified water | Rest | Rest | Rest | Rest | Rest |

<Test Example 4> Measurement of Size of Oil Phase 2

1. Evaluation Method

The average (Z-average) diameter of the oil phase in the compositions of Preparation Example 3 was investigated using a NanoBrook Omni particle size analyzer (Malvern-Panalytical). The result is shown in Table 6 and FIG. 4.

TABLE 6

| (Unit: nm) | | | | | |
|---|---|---|---|---|---|
| | Ex. 12 | Ex. 13 | Ex. 14 | Ex. 15 | Ex. 16 |
| Average diameter | 168.7 | 173.6 | 213.6 | 213.8 | 224 |

2. Evaluation Result

As seen from Table 6 and FIG. 4, compositions with the average (Z-average) diameter of the oil phase of 168.7 nm, 173.6 nm, 213.6 nm, 213.8 nm and 224 nm could be obtained by changing the contents of the ginseng seed oil and the ginseng nanopowder precursor. Through this, it can be seen that the size of the oil phase of the composition can be controlled by controlling the contents of the ginseng seed oil and the ginseng nanopowder precursor in aqueous counter collision.

1. Evaluation Method

Sixty adults aged 45 years on average were asked to apply the compositions of Examples and Comparative Examples described in Table 7 and foreign body sensation resulting from coagulation was evaluated using 9-point scales (Evaluation standards are described in Table 8.). The total score is given in Table 9.

TABLE 7

| (Unit: nm) | Ex. 12 | Ex. 13 | Ex. 14 | Ex. 15 | Ex. 16 | Ex. 17 | Comp. Ex. 8 | Comp. Ex. 9 |
|---|---|---|---|---|---|---|---|---|
| Average diameter | 168.7 | 173.6 | 213.6 | 213.8 | 224 | 500 | 800 | 1000 |

TABLE 8

| Evaluation after use | Never satisfactory | | | | Moderate | | | | Very satisfactory |
|---|---|---|---|---|---|---|---|---|---|
| 1 Viscosity/concentration: degree of thickness of contents | 1 | 2 | 3 | 4 | 5 | 6 | 7 | 8 | 9 |
| 2 Mildness: mildness with no skin irritation | 1 | 2 | 3 | 4 | 5 | 6 | 7 | 8 | 9 |
| 3 Moistness: moistness of skin upon application | 1 | 2 | 3 | 4 | 5 | 6 | 7 | 8 | 9 |
| 4 Moisturization: maintenance of moistness after application | 1 | 2 | 3 | 4 | 5 | 6 | 7 | 8 | 9 |
| 5 Elasticity: skin elasticity after application | 1 | 2 | 3 | 4 | 5 | 6 | 7 | 8 | 9 |
| 6 Absorption: clean absorption without residues | 1 | 2 | 3 | 4 | 5 | 6 | 7 | 8 | 9 |
| 7 Freshness: lack of stickiness during application or after absorption | 1 | 2 | 3 | 4 | 5 | 6 | 7 | 8 | 9 |
| 8 Feeling of skin health | 1 | 2 | 3 | 4 | 5 | 6 | 7 | 8 | 9 |

TABLE 9

| | Ex. 12 | Ex. 13 | Ex. 14 | Ex. 15 | Ex. 16 | Ex. 17 | Comp. Ex. 8 | Comp. Ex. 9 |
|---|---|---|---|---|---|---|---|---|
| Feeling after use | 64 | 64 | 61 | 62 | 59 | 58 | 41 | 35 |

2. Evaluation Result

From Table 9, it can be seen that the compositions of Examples 12-17 provide superior feeling after use. However, Comparative Examples 8 and 9, wherein the average diameter of the oil phase exceeds the desired range, do not provide good feeling after use.

The present disclosure relates at least to the following aspects and includes at least the following embodiments.

[Aspect 1] A nanoemulsion cosmetic composition including an oil phase and an aqueous phase, wherein the oil phase contains a ginseng nanopowder and an oil swollen by the ginseng nanopowder, the composition does not contain an additional surfactant, and the ginseng nanopowder is distributed uniformly in the composition.

[Aspect 2] The composition according to aspect 1, wherein the ginseng nanopowder is obtained from ginseng root.

[Aspect 3] The composition according to aspect 1 or aspect 2, wherein the oil is ginseng seed oil and the composition is a whole cosmetic composition.

[Aspect 4] The composition according to any of aspects 1 to 3, wherein the composition is an oil-in-water type.

[Aspect 5] The composition according to any of aspects 1 to 4, wherein the oil phase is contained in an amount of 4-20 wt % based on the total weight of the composition.

[Aspect 6] The composition according to any of aspects 1 to 5, wherein the oil phase has an average diameter of 500 nm or less.

[Aspect 7] The composition according to any of aspects 1 to 6, wherein the oil phase is contained in an amount of 2.5-15 wt % based on the total weight of the composition.

[Aspect 8] The composition according to any of aspects 1 to 7, wherein the ginseng nanopowder is contained in an amount of more than 0 wt % and 5 wt % or less based on the total weight of the composition.

[Aspect 9] The composition according to any of aspects 1 to 8, wherein the ginseng nanopowder and the oil are contained at a ratio of 1:1-3 based on weight.

[Aspect 10] A method for preparing the nanoemulsion cosmetic composition according to any of aspects 1 to 9, which includes preparing an emulsion through collision dispersion of water, an oil and a ginseng nanopowder precursor.

[Aspect 11] The method according to aspect 10, wherein the collision dispersion is achieved by spraying a solution wherein water, an oil and a ginseng nanopowder precursor are dispersed using opposing nozzles.

[Aspect 12] The method according to aspect 11, wherein the collision pressure of the spraying is 180-200 MPa.

[Aspect 13] The method according to aspect 10 or aspect 11, wherein the oil is ginseng seed oil.

[Aspect 14] The method according to any of aspects 10 to 13, wherein the ginseng nanopowder precursor comprises particles with a volume-based particle size distribution, D90, measured by laser diffractometry of less than 16 μm.

Although the present disclosure has been described through specific exemplary embodiments, various changes or modifications can be made without departing from the spirit and scope of the present disclosure. Accordingly, such changes or modifications will be included within the scope of the appended claims.

What is claimed is:

1. A nanoemulsion cosmetic composition comprising an oil phase and an aqueous phase, wherein
    the oil phase comprises a ginseng nanopowder and an oil swollen by the ginseng nanopowder,
    the composition does not comprise a synthetic surfactant,
    the ginseng nanopowder is distributed uniformly in the composition,
    wherein the oil is ginseng seed oil, and
    wherein the composition is an oil-in-water composition,
    wherein the ginseng nanopowder is contained in an amount of more than 0 wt % and 5 wt % or less based on the total weight of the composition, and
    wherein the ginseng nanopowder and the oil are contained at a ratio of 1:1-3 based on weight.

2. The composition according to claim 1, wherein the ginseng nanopowder is obtained from ginseng root.

3. The composition according to claim 1, wherein the composition is a whole cosmetic composition.

4. The composition according to claim 1, wherein the oil phase is contained in an amount of 4-20 wt % based on the total weight of the composition.

5. The composition according to claim 1, wherein the oil phase has an average diameter of 500 nm or less.

6. The composition according to claim 1, wherein the oil phase is contained in an amount of 2.5-15 wt % based on the total weight of the composition.

7. A method for preparing the nanoemulsion cosmetic composition according to claim 1, comprising preparing an emulsion through collision dispersion of water, an oil and a ginseng nanopowder precursor.

8. The method according to claim 7, wherein the collision dispersion is achieved by spraying a solution wherein water, an oil and a ginseng nanopowder precursor are dispersed using opposing nozzles.

9. The method according to claim 8, wherein the collision pressure of the spraying is 180-200 MPa.

10. The method according to claim 7, wherein the oil is ginseng seed oil.

11. The method according to claim 7, wherein the ginseng nanopowder precursor comprises particles with a volume-based particle size distribution, D90, measured by laser diffractometry of less than 16 μm.

* * * * *